United States Patent [19]
Arnal et al.

[11] Patent Number: 5,863,906
[45] Date of Patent: Jan. 26, 1999

[54] COMPOSITION BASED ON AMINO ACIDS INTENDED FOR THE TREATMENT OF SEPSIS OR OF AN ATTACK BRINGING ABOUT AN INFLAMMATORY REACTION, IN ANIMALS AND MAN

[75] Inventors: Maurice Arnal, Romagnat; Francis Rose, Paris; Denis Breuille, Saint-Saturnin; Christiane Obled, St. Amant Tallende, all of France

[73] Assignee: Nestec S.A., Vevey, Switzerland

[21] Appl. No.: 896,611

[22] Filed: Jul. 18, 1997

Related U.S. Application Data

[63] Continuation of Ser. No. 647,124, May 9, 1996, Pat. No. 5,756,481.

[30] Foreign Application Priority Data

Oct. 28, 1993 [FR] France .................................. 93 12883

[51] Int. Cl.$^6$ .................................................. A01N 43/04
[52] U.S. Cl. .............................. 514/49; 514/68; 424/173; 424/185.1
[58] Field of Search ....................... 514/49, 68; 424/1.73, 424/185.1

[56] References Cited

U.S. PATENT DOCUMENTS 4,491,589  1/1985  Dell et al. .............................. 424/274

OTHER PUBLICATIONS

Gottschlich, M. M. et al. Differential Effects of Three Enteral Dietary Regimens of Selected Outcome Variables in Burn Patients, Journal of Parenteral and Enteral Nutrition, vol. 14, No. 3, May/Jun. 1990, pp. 225–236.
The Merck Index, An Encyclopedia of Chemicals and Drugs, 9th Ed., p. 364, Entry No. 2780, 1976.
Dictionary of Drugs, Elks et al., p. 339 Entry No. C–00654, 1990.
Derwent Patent Abstract No. 83–754330, Aug. 31, 1983.
Derwent Patent Abstract No. 84–199494, Apr. 7, 1984.
Derwent Patent Abstract No. 87–106533, Aug. 15, 1986.
Derwent Patent Abstract No. 87–192382, Jul. 2, 1987.
Derwent Patent Abstract No. 94–250610, Aug. 8, 1991.
Derwent Patent Abstract No. 93–008942, Nov. 19, 1992.
Derwent Patent Abstract No. 94–250610, Aug. 10, 1994.

*Primary Examiner*—Duc Troung
*Attorney, Agent, or Firm*—Hill & Simpson

[57] ABSTRACT

Compositions and methods intended to be administered enterally or parenterally for treating sepsis. The composition containing, in a biologically and nutritionally acceptable medium, at least free cysteine or cysteine in the form of a precursor, prodrug, protein or peptide hydrolysate, in a proportion of pharmacologically active cysteine greater than the proportion of cysteine present in a nutritional composition corresponding to the requirements of a healthy man, the proportion of cysteine being determined with respect to all the amino acids present in the composition.

25 Claims, No Drawings

COMPOSITION BASED ON AMINO ACIDS INTENDED FOR THE TREATMENT OF SEPSIS OR OF AN ATTACK BRINGING ABOUT AN INFLAMMATORY REACTION, IN ANIMALS AND MAN

This is a continuation of application Ser. No. 08/647,124, filed May 9, 1996, now U.S. Pat. No. 5,756,481.

BACKGROUND OF THE INVENTION

The present invention relates to compositions based on amino acids for preventing and/or reducing tissue damage brought about by multiple metabolic dysfunctions which appear, especially as a result of a sepsis.

Infection may be independent of any other pathology, but infection most commonly occurs in man after a surgical operation or is associated with a trauma, a burn, diabetes, a cirrhosis, a neoplasm, or the like. Infection may also occur during treatment with immunosuppression, cytolytic or cytostatic agents. Septic illnesses are also strongly correlated with a state of malnutrition, very especially in young children and in elderly people. Such illnesses are also found in animals such as domestic animals and especially in industrial stockraising (pigs, chickens, and the like).

The metabolic response to infection is complex and, up to the present, very many issues still remain unexplained. This complexity results in particular from the participation of many factors: modification in the supplies of the substrates to the various organs and in their use, variation in the sensitivity and the reactivity of the tissues to the hormones, for example resistance to insulin, change in blood flow rates, participation of many mediators such as PAF, or cytokines (interleukins, TNF, and the like), the pharmacological effects of which may be in conflict according to the tissue under consideration.

The response to infection is dynamic, with several phases whose intensity and duration depend on the severity of the attack and on the time at which infection occurs with respect to the attack. Three periods are usually distinguished (Cuthbertson, 1942). The "ebb phase"—the 24 hours after the attack which is characterized by a rapid mobilization of the energetic substrates and a reduced metabolic activity. The ebb phase is followed by the "flow phase", the duration of which varies from a few days to 2 to 3 weeks. This period sees a metabolic activity increase with the result of a general catabolism of the tissues, in particular of the muscle. The last phase, in survivors, corresponds to the convalescence, which is anabolic.

The present invention is more particularly targeted at treating or preventing by nutritional compositions the dysfunctions which take place in the first two phases. These phases are characterized by the existence of an anorexia and a hypermetabolic response which is reflected clinically by the weight loss and especially a wasting away in muscle proteins, by an inflammatory state, the existence of a tachycardia, a hyperventilation, an increased oxygen consumption, a disfunction of the immune system, and the like.

Accelerated loss in proteins from the muscle is used to deal with:

—the increased requirements for glucose of the body by means of hepatic neoglucogenesis and for glutamine, an essential energy source for the cells of the intestinal mucous membrane or for the rapid multiplication cells of the immune system, —the amino acid requirements for the increased protein syntheses of several organs, in particular of inflammatory proteins in the liver.

The actions of the hormones and of certain mediators, such as α-TNF, have been the subject and still form the subject of many evaluations. Although certain mechanisms are beginning to be better explained, with respect to the specific nutritional requirements and more particularly those which concern amino acids, very little is known in the case of sepsis or of post-attack inflammatory reactions.

SUMMARY OF THE INVENTION

The present invention provides a method and composition for treating sepsis.

To this end, the present invention provides, in an embodiment, a composition comprising a biologically and nutritionally acceptable medium and including at least one component for providing cysteine chosen from the group consisting of free cysteine, cysteine precursor, cysteine prodrug, protein including cysteine and peptide hydrolysate containing cysteine, the component for providing cysteine being present in a proportion so that the pharmacologically active cysteine that is provided to an individual that ingest the composition is greater than the proportion of cysteine present in a nutritional composition that corresponds to the requirements of a healthy man, the proportion of cysteine being determined with respect to all the amino acids present in the composition.

In an embodiment, the cysteine in the pharmacologically active form is present in a proportion equal to or greater than 3% with respect to all the amino acids present in the composition.

In an embodiment, the amount of nitrogen from the cysteine is greater than or equal to 2.15% with respect to the total amount of nitrogen.

In an embodiment, the composition includes threonine in proportions equal to or greater than 5% by weight with respect to the other amino acids that are present in the composition.

In an embodiment, the composition includes serine in proportions equal to or greater than 12% by weight with respect to the other amino acids that are present in the composition.

In an embodiment, the composition includes at least aspartic acid in proportions greater than or equal to 10%, these proportions being determined with respect to the amount of amino acid present in the composition.

In an embodiment, the composition includes at least asparagine in proportions greater than or equal to 10%, these proportions being determined with respect to the amount of amino acid present in the composition.

In an embodiment, the composition includes leucine, isoleucine, valine, tryptophan, phenylalanine, lysine, methionine and threonine.

In an embodiment, the composition includes glycine.

In an embodiment, the composition includes arginine.

In an embodiment, the composition includes taurine.

In an embodiment, the composition includes glutamine.

In an embodiment, the amino acids are present in a free form.

In an embodiment, the composition contains, per one liter:

| | |
|---|---|
| Leucine | 5 to 12 g/l |
| Isoleucine | 3 to 10 g/l |
| Valine | 5 to 10 g/l |

-continued

| | |
|---|---|
| Tryptophan | 1.0 to 3 g/l |
| Phenylalanine | 1.5 to 7 g/l |
| Lysine | 2 to 7 g/l |
| Methionine | 1.5 to 5 g/l |
| Threonine | 3.0 to 7 g/l. |

In an embodiment, cystine is present in the form of a prodrug.

In an embodiment, the composition includes L-oxothiazolidine-carboxylic acid.

In an embodiment, the composition includes salts of L-oxothiazolidine-carboxylic acid.

In an embodiment, the composition is in the form of a solution.

In an embodiment, the composition is provided as a complete nutritional composition intended for parenteral administration and includes a carbohydrate calorie source, a lipid calorie source, electrolytes, trace elements and vitamins.

In an embodiment, the composition is provided in the form of a nutritional enteral composition a calorie source, a carbohydrate, a lipid calorie source, electrolytes, trace elements and vitamins.

In an embodiment, the composition is provided in the form of a powder which can be rehydrated at the time of administration.

The present invention also provides a method for preventing or decreasing tissue damage brought about by metabolic dysfunctions.

The present invention also provides a method of treating sepsis or to an attack bringing about an inflammatory reaction.

Additional features and advantages of the present invention are described in, and will be apparent from, the detailed description of the presently preferred embodiments.

DETAILED DESCRIPTION OF THE PRESENTLY PREFERRED EMBODIMENTS

The inventors have determined that the sudden stimulation of the syntheses of a large number of inflammatory and defensive proteins, vital for the body, secreted in low amounts in the normal physiological situation, rich in certain amino acids is required in particular, in the case of sepsis. During this acute phase, in view of the state of anorexia of the patients or the animals, the synthesis of these proteins implies that the body degrades significant amounts of muscle proteins or other proteins, in order to have available a sufficient amount of these amino acids. The increased consumption of glutamine, as an energy source, by the digestive system during various attacks, is an illustration thereof.

The hepatic proteins of inflammation, such as C-reactive protein, $\alpha_1$-1-antichymotrypsin, $\alpha_1$-acid glycoprotein, fibrinogen, haptoglobulin, $\alpha_2$-macroglobulin (in rats) or metallothioneins, contain a high percentage of cysteine, serine, aspartic acid, asparagine and threonine compared with those of muscle proteins. Threonine, aspartic acid and asparagine are amino acids to which are bonded the constituent carbohydrate units of these various glycoproteins.

During the defensive reactions, as a result of the state of anorexia, the body, in order to synthesize these various vital proteins, must significantly degrade its muscle proteins in order to cover these specific requirements. This is all the more true since myofibril proteins, the proteins of the inflammatory reaction, generally have short half-lives.

By providing for the amino acid requirements not only makes it possible for the body to improve the syntheses of vital proteins but also makes it possible to avoid the loss of muscle proteins. As the body does not have reserve proteins, any amount of lost proteins corresponds to a loss of function. The reduction in the muscle proteins not only leads to a detrimental change in the respiratory capacities of the patient but also in his motor capacities. There follows a long period of convalescence, given that the regeneration of myofibril proteins is slow. By providing the necessary requirements this leads to a shorter sickness time and makes it possible to shorten the period of hospitalization. It also makes possible a better protection return for domestic animals.

It has also been determined that, during the period of shock due to sepsis, with the existence of a persistent hypermetabolism, there exists an abundant production of free radicals. The harmful effects of free radicals have been widely described. To control these oxidizing processes, the body has available antioxidizing substances and "radical traps." Glutathione, a tripeptide composed of glycine, glutamic acid and cysteine, is one of the most abundant of these substances. The increased requirement for this derivative involves, for the body, having available for its synthesis a sufficient amount of the three amino acids which constitute glutathione.

The loss of glutathione, at the cell level, has deleterious metabolic consequences for the body: in addition to its role as a free radical captor, glutathione is involved in many reactions of the metabolism (coenzyme of enzymatic reactions, synthesis of deoxyribonucleotides, metabolism of xenobiotics, intracellular reducing agent) and it is itself a cysteine reserve, directly available for protein synthesis.

The inventors have discovered, after developing a sepsis model in rats, consisting of a single injection of living bacteria (*E. coli*) which keeps the animals in a catabolic situation lasting several days, that the requirement for certain amino acids had increased.

It was determined that, during the induced sepsis, there is observed in the septic animals, as compared to "pair-fed" animals, a significant loss in weight. This weight lost, lasted two or three days, with the institution of a severe anorexia. It was also found in the septic animals that there was a high level of circulating $\alpha$-TNF greater than 10 ng/ml, a plasma content of acid $\alpha_1$-glycoprotein multiplied by 20 to 60, a hyperglycaemia (1.82 g/l) and a hyperinsulinaemia (34.7 $\mu$u/ml).

Measurements of protein synthesis, estimated by the large dose technique, have shown, still with respect to "pair-fed" animals, that, in the liver, the rate of synthesis had increased from 1.8 to 2.7 times whereas, in the muscle, it had decreased by 30%. In the latter tissue, an increase in proteolysis is observed.

The protein synthesis of the whole body, less that of the liver, is increased despite a large decrease in muscle syntheses. This implies that, in other organs, the syntheses are stimulated. It was possible, in particular, to observe an increase in protein synthesis in the spleen and lungs.

The study of the fixation and oxidation balances of the amino acids during this infection model has made it possible, in fact, to determine an increased requirement for a number of essential and nonessential amino acids, and more particularly in the liver. The protein content of the liver of the infected rats increases by 42% compared with the pair-fed controls. The inventors were able to observe more particularly an increase in the concentration of cysteine of the order of 74%.

The analysis of the amino acids content of the whole body showed a large decrease in the infected animals, except for the cysteine/cystine combination which increases significantly by 9% with respect to the pair-fed controls and for certain amino acids (threonine and arginine), which are maintained at the same level. This indicates a saving of these amino acids, since the infected rats catabolize 3.7 and 54% less threonine and cysteine respectively than the pair-fed controls, in contrast to all the other indispensable amino acids which show increased oxidations of 10 to 30% during the infection.

Analysis of the distribution of radioactivity in the different tissues after injection of L-$[^{35}S]$ cysteine into rats in the above-mentioned model of infection revealed an increased utilization of cysteine to synthesize the proteins of the inflammatory reaction and glutathione. In effect, the radioactivity incorporated per gram of protein in the spleen and in the plasma proteins minus albumin increases by 70% in infected animals relative to their pair-fed controls. The percentage of the injected dose occurring in a fraction mainly containing cysteine and glutathione is, respectively, 1.9 and 4 times as high in the liver and the spleen of infected animals compared with pair-fed controls.

The effect on weight loss of supplementing diets with amino acids confirmed the inventors' belief for an increased requirement for certain amino acids during an infection. Three groups of animals receiving diets with equal nitrogen contents were compared: a control group (group C), a group receiving a diet supplemented with threonine, serine, aspartic acid, asparagine and arginine (group AA) and a group receiving a diet supplemented with threonine, serine, aspartic acid, asparagine, arginine and cysteine (group Cys). These supplementations enabled the weight loss to be limited and the resumption of growth of the infected animals to be accelerated. Ten days after infection, the animals' weight was 15%, 8% and 2.5% lower than their initial weight in groups C, AA and Cys, respectively. Increasing the cysteine content of the diet from 0.8% to 6.7% led to an approximately 35% reduction in the nitrogen excretion of the infected animals relative to their pair-fed controls in the days following infection. In this same study, supplementation of the diet with cysteine enabled the glutathione concentration in the liver to be normalized, the latter concentration being decreased by a factor of the order of 25% with the diet containing only 0.8% of cysteine.

These results have made it possible for the inventors to establish that, during sepsis in particular and more generally during the triggering of highly catabolic and hypermetabolic situations, the requirements for cysteine and, on a lesser scale, for threonine, serine, aspartic acid and asparagine, are markedly increased.

The present invention provides compositions of amino acids present in proportions such that they provide the specific requirements for amino acids and make it possible to avoid or to prevent the loss of significant mass of muscle proteins.

The present invention provides an amino acids composition, intended to be administered orally, enterally or parenterally, which makes it possible to solve the above-identified problems.

In another embodiment, the invention provides the use of a composition of amino acids, for the purpose of treating tissue damage brought about by metabolic dysfunctions which appear in particular as a result of sepsis.

In another embodiment, the invention provides a method for treatment and prevention of tissue damage brought about by metabolic dysfunctions which appear especially as a result of a sepsis.

The composition based on amino acids intended to be administered orally, enterally or parenterally, in accordance with the invention, contains, in a biologically and nutritionally acceptable medium, at least free cysteine or cysteine in the form of a prodrug or proteins or hydrolysates which are rich in cysteine, in a proportion of pharmacologically active cysteine greater than the proportion of cysteine present in a nutritional composition corresponding to the requirements of a healthy man. The proportion of cysteine is determined with respect to all the amino acids present in the composition.

In a preferred embodiment of the invention, cysteine, in the pharmacologically active form, is present in a proportion equal to or greater than 3% with respect to all the amino acids present in the composition.

In an embodiment of the present invention, the composition of amino acids in accordance with the invention additionally contains at least threonine in proportions equal to or greater than 5% and/or at least serine in proportions equal to or greater than 12% and/or at least aspartic acid or asparagine in proportions equal to or greater than 10%, these proportions being determined with respect to the amount of amino acids present in the composition.

In a preferred embodiment, the present invention provides compositions as defined above containing the 8 essential amino acids, namely leucine, isoleucine, valine, tryptophan, phenylalanine, lysine, methionine and threonine.

According to another embodiment of the invention the composition also contains glycine and/or arginine.

The composition in accordance with the invention can also contain taurine and/or glutamine.

The compositions in accordance with the invention are in an embodiment provided in a solution form, which is a mixture of amino acids. In an embodiment, the compositions can optionally be used in the form of their pharmaceutically acceptable salts, in a medium consisting generally of distilled water.

The compositions in accordance with the invention can, in an embodiment, contain, per 1 liter of amino acids solutions, the following constituents in the following amounts:

| | |
|---|---|
| Leucine | 5 to 12 g/l |
| Isoleucine | 3 to 10 g/l |
| Valine | 5 to 10 g/l |
| Tryptophan | 1.0 to 3 g/l |
| Phenylalanine | 1.5 to 7 g/l |
| Lysine | 2 to 7 g/l |
| Methionine | 1.5 to 5 g/l |
| Threonine | 3.0 to 7 g/l |

This composition can optionally contain serine in proportions from 2.5 to 6 g/l, aspartic acid in proportions from 1.5 to 4 g/l, glycine in proportions from 3 to 7 g/l, arginine in proportions between 5 and 10 g/l, taurine in proportions between 1 and 4 g/l, and glutamine in proportions greater than or equal to 4 g/l.

Pursuant to the present invention, cysteine is present in this composition in proportions equal to or greater than 3% with respect to the total amount of amino acids present. Preferably, the cysteine is present in the composition at a level of between 3 to about 10% of the total amino acids present.

According to another preferred embodiment of the invention, threonine, as already shown above, is present in proportions equal to or greater than 5% and is preferably present at a level of between 5 to about 12% with respect to the total amount of amino acids present.

Serine, when it is present, is preferentially present in proportions equal to or greater than 12% and preferably between 12 to about 16% with respect to the total weight of amino acids present. Aspartic acid or asparagine, when they are present, are preferably present in proportions equal to or greater than 10% to about preferably between 10 and 15% with respect to the total weight of amino acids present.

Cysteine, used in accordance with the invention, can be used in a prodrug form or in the form of a pharmaceutically acceptable salt, such as in the L-oxothiazolidinecarboxylic acid form, especially when it is desired to avoid maintaining high cysteine plasma levels. It is well understood that it is possible to use other cysteine precursors or derivatives which can be converted to cysteine inside cells. Cysteine can be used in the combined form with other amino acids such as in the protein or peptide form.

The amounts of prodrug or cysteine precursors, peptide or protein are determined on the basis of the cysteine which is capable of being released from these derivatives.

It is also possible to use the other amino acids mentioned above in the form of precursors or prodrugs, such as, for example, in the dipeptide form, especially in the case of aspartic acid and/or of asparagine.

The compositions in accordance with the invention can be provided not only in an aqueous solution form but also in other forms. Thus it is that cysteine can be administered simply by modifying existing enteral oral formula by introducing therein the amount of cysteine compatible with the proportions in accordance with the invention.

The supplementation of cysteine can also be carried out in preparations intended for oral or enteral nutrition. It can be carried out, in this case, by the use of proteins or peptide hydrolysates which are naturally rich in cysteine/cystine.

The cysteine level must, in this case, also be present in amounts greater than the proportion of cysteine present in a composition intended for a healthy man; this amount is determined with respect to all the amino acids present in the free or combined form. It is also possible to express the necessary amount by taking account of the nitrogen content contained in the cysteine or of these precursors and that of the total amount of nitrogen in the composition. The percentage represents in this case the amount of nitrogen from the cysteine with respect to the total nitrogen present.

Cysteine bonded in a protein or a peptide hydrolysate is preferably present in proportions equal to or greater than 3% with respect to all the amino acids present in the free or bonded form in the composition.

When it is expressed as nitrogen content, the amount of nitrogen from free cysteine or cysteine in the form of one of its precursors, prodrug, protein or peptide hydrolysate is greater than or equal to 2.15% with respect to the total nitrogen.

The compositions of the present invention can be provided in the form of a complete nutritional composition intended for parenteral administration. Such preparations can contain, besides the amino acids or their derivates (peptides), carbohydrate (glucose, fructose, sorbitol, and the like) and/or lipid (fatty acid triglycerides) calorie sources. The lipids can contain long chains, medium chains, or short chains, triglycerides. The composition can also contain electrolytes, trace elements and vitamins. In these nutritional compositions, cysteine or its precursors will be present in proportions greater than 3% with respect to the amount of amino acids present in the nutritive composition.

The parenteral composition can be provided in the form of an aqueous solution or non-aqueous solution, suspension or emulsion.

When the composition is provided in the form of a nutritional composition intended for the oral or enteral route cysteine will be present in proportions greater than 3% with respect to the amount of amino acids present in the nutritive composition. The supplementation of cysteine or of other amino acids mentioned above is obtained either with the amino acid itself, with a prodrug or with proteins or peptide hydrolysates which are particularly rich in the amino acid under consideration (for example cysteine). This composition, besides proteins, amino acids and peptides, can contain carbohydrate (in the form of various hydrochlorides) and/or lipid (triglycerides of fatty acids containing long or medium chains, introduced in the form of oils of various origins) calorie sources, electrolytes, trace elements and vitamins.

Cysteine can also be premixed with the other amino acids which can be used in the compositions in accordance with the invention. The cysteine can also be provided in the form of an aseptic powder which can be rehydrated at the time of administration or can be stored in the form of a frozen or refrigerated concentrate which is defrosted and mixed to the suitable concentration at the time of use.

These compositions can be administered by devices known in the methods of oral, parenteral or enteral administration.

Another subject of the invention consists of a method for preventing or decreasing tissue damage brought about by metabolic dysfunctions. The treatment is carried out using the compositions set forth above parenterally or enterally.

Another subject of the invention is the treatment of tissue damage brought about by metabolic dysfunctions which appear in particular as a result of sepsis, by administering, parenterally and enterally, to man or animals a sufficient amount of cysteine or of a functional analogue as a defined above, in amounts which are pharmacologically active and greater than the amount of cysteine present in a nutritional composition corresponding to the requirements of a healthy man or animal.

The administration is more particularly carried out orally, parenterally or enterally. The amount of cysteine administered is equal to or greater than 3% with respect to the total amount of amino acids administered and is preferably between 3% and 10%.

By way of example, and not limitation, the following examples are provided.

EXAMPLES 1 AND 2

The following amino acid solutions are prepared:

| | | |
|---|---|---|
| Leu | 7.2 g/l | 7.2 g/l |
| Ile | 5.6 g/l | 5.6 g/l |
| Val | 5.6 g/l | 5.6 g/l |
| Trp | 1.2 g/l | 1.2 g/l |
| Phe | 3.2 g/l | 3.2 g/l |
| Lys | 3.2 g/l | 3.2 g/l |
| Met | 2 g/l | 2 g/l |
| Thr | 4 g/l | 6 g/l |

-continued

| | | |
|---|---|---|
| Asp | 8 g/l | 8.5 g/l |
| Glu | 2.4 g/l | 2.4 g/l |
| Ser | 9.8 g/l | 9.8 g/l |
| Gly | 5.9 g/l | 5 g/l |
| Ala | 6.2 g/l | 5.8 g/l |
| Cys | 2.5 g/l | 4 g/l |
| Orn | 2.4 g/l | — |
| Tyr | 0.4 g/l | 0.4 g/l |
| His | 3.2 g/l | 3 g/l |
| Arg | 4.6 g/l | 4.6 g/l |
| Pro | 3.2 g/l | 3.2 g/l |
| Distilled water q.s. for | 1 l | |
| AAT | 80.2 g/l | 80.7 g/l |

EXAMPLE 3

The following amino acid solution is prepared:

| | |
|---|---|
| Leu | 6 g/l |
| Ile | 4.5 g/l |
| Val | 4.5 g/l |
| Trp | 1.2 g/l |
| Phe | 3 g/l |
| Lys | 3 g/l |
| Met | 2 g/l |
| Thr | 6 g/l |
| Asp | 8.5 g/l |
| Gln | 8 g/l |
| Ser | 9.8 g/l |
| Gly | 4.8 g/l |
| Ala | 4 g/l |
| Cys | 4 g/l |
| Orn | — |
| Tyr | 0.4 g/l |
| His | 3 g/l |
| Arg | 4 g/l |
| Water q.s. for | 1 l |
| AAT | 81.1 g/l |

EXAMPLE 4

The following amino acid solution is prepared:

| | |
|---|---|
| Leu | 12 g/l |
| Ile | 9.3 g/l |
| Val | 9.3 g/l |
| Trp | 2 g/l |
| Phe | 5.33 g/l |
| Lys | 5.33 g/l |
| Met | 3.33 g/l |
| Thr | 10 g/l |
| Asp | 14.16 g/l |
| Glu | 4 g/l |
| Ser | 16.8 g/l |
| Gly | 8.33 g/l |
| Ala | 10 g/l |
| Cys | 6.66 g/l |
| Orn | — |
| Tyr | 0.5 g/l |
| His | 5 g/l |
| Arg | 7.6 g/l |
| Pro | 5.18 g/l |
| Water q.s. for | 1 l |
| AAT | 134.17 g/l |

EXAMPLES 5 AND 6

The following amino acid solutions are prepared:

| | | |
|---|---|---|
| Leu | 7.2 g/l | 7.2 g/l |
| Ile | 5.6 g/l | 5.6 g/l |
| Val | 5.6 g/l | 5.6 g/l |
| Trp | 1.2 g/l | 1.2 g/l |
| Phe | 3.2 g/l | 3.2 g/l |
| Lys | 3.2 g/l | 3.2 g/l |
| Met | 2 g/l | 2 g/l |
| Thr | 4 g/l | 6 g/l |
| Asp | 8 g/l | 8.5 g/l |
| Glu | 2.4 g/l | 2.4 g/l |
| Ser | 9.8 g/l | 9.8 g/l |
| Gly | 5.6 g/l | 5 g/l |
| Ala | 6 g/l | 5.8 g/l |
| OTC° | 2.6 g/l | 4 g/l |
| Orn | 2.4 g/l | — |
| Tyr | 0.4 g/l | 0.4 g/l |
| His | 3.2 g/l | 3 g/l |
| Arg | 4.8 g/l | 4.6 g/l |
| Pro | 3.2 g/l | 3.2 g/l |
| Water q.s. for | 1 l | |
| AAT | 80.4 g/l | 80.7 g/l |

° 4-Oxothiazolidinecarboxylic acid or in the salt form.

EXAMPLE 7

The following amino acid solution is prepared:

| | |
|---|---|
| Leu | 6 g/l |
| Ile | 4.5 g/l |
| Val | 4.5 g/l |
| Trp | 1.2 g/l |
| Phe | 3 g/l |
| Lys | 3 g/l |
| Met | 2 g/l |
| Thr | 6 g/l |
| Asp | 8.5 g/l |
| Gln | 7.8 g/l |
| Ser | 9.8 g/l |
| Gly | 5 g/l |
| Ala | 4 g/l |
| OTC° | 4 g/l |
| Orn | — |
| Tyr | 0.4 g/l |
| His | 3 g/l |
| Arg | 4 g/l |
| Pro | 3 g/l |
| Water q.s. for | 1 l |
| AAT | 81.1 g/l |

° 4-Oxothiazolidinecarboxylic acid or in the salt form.

EXAMPLE 8

The following amino acid solution is prepared:

| | |
|---|---|
| Leu | 12 g/l |
| Ile | 9.3 g/l |
| Val | 9.3 g/l |
| Trp | 2 g/l |
| Phe | 5.33 g/l |
| Lys | 5.33 g/l |
| Met | 3.33 g/l |
| Thr | 10 g/l |
| Asp | 14.16 g/l |
| Gln | 4 g/l |
| Ser | 16 g/l |
| Gly | 8.33 g/l |
| Ala | 10 g/l |
| OTC° | 6.66 g/l |

-continued

| | |
|---|---|
| Orn | — |
| Tyr | 0.5 g/l |
| His | 5 g/l |
| Arg | 7.6 g/l |
| Pro | 5.33 g/l |
| Water q.s. for | 1 l |
| AAT | 134.17 g/l |

° 4-Oxothiazolidinecarboxylic acid or in the salt form.

EXAMPLE 9

The following amino acid solution is prepared:

| | |
|---|---|
| Leu | 6 g/l |
| Ile | 5 g/l |
| Val | 5 g/l |
| Trp | 1.2 g/l |
| Phe | 3 g/l |
| Lys | 3 g/l |
| Met | 2 g/l |
| Thr | 6 g/l |
| Asp | 8.5 g/l |
| Ser | 9.6 g/l |
| Cys | 5 g/l |
| Ala—Gln | 15 g/l |
| Gly | 5 g/l |
| Arg | 4 g/l |
| Water q.s. for | 1 l |
| AAT | 78.3 g/l |

EXAMPLE 10

The following amino acid solution is prepared:

| | |
|---|---|
| Leu | 6 g/l |
| Ile | 5 g/l |
| Val | 5 g/l |
| Trp | 1.2 g/l |
| Phe | 3 g/l |
| Lys | 3 g/l |
| Met | 2 g/l |
| Thr | 6 g/l |
| Asp | 8.5 g/l |
| Ser | 9.6 g/l |
| OTC° | 5 g/l |
| Ala—Gln | 15 g/l |
| Gly | 5 g/l |
| Arg | 4 g/l |
| Water q.s. for | 1 l |
| AAT | 78.3 g/l |

° 4-Oxothiazolidinecarboxylic acid or in the salt form.

EXAMPLE 11

Composition (for 1000 ml) intended for oral or enteral administration

| | | |
|---|---|---|
| Proteins | 58.2 g | (in the form of small casein and whey peptides) |
| Cysteine | 4.9 g | |
| Lipids | 52 g | (medium chain triglycerides, soya oil, and the like) |
| Glucides | 158 g | (maltodextrins and starch) |
| Inorganics | | |
| Sodium | 1000 mg | |

-continued

| | |
|---|---|
| Potassium | 1660 mg |
| Calcium | 450 mg |
| Phosphorus | 500 mg |
| Magnesium | 330 mg |
| Iron | 13.3 mg |
| Zinc | 13.3 mg |
| Manganese | 2.7 mg |
| Copper | 1.3 mg |
| Chlorides | 2500 mg |
| Iodine | 100 mg |
| Vitamins | |
| A | 1064 mg |
| E | 20 mg |
| $B_1$ | 2 mg |
| $B_2$ | 2 mg |
| $B_5$ | 6.7 mg |
| $B_6$ | 2.6 mg |
| C | 133 mg |
| PP | 26.6 mg |
| $B_{12}$ | 3 mg |
| Folic acid | 333 mg |
| Biotin | 133 mg |
| Choline | 266 mg |

The same proportion of cysteine can also be supplied by a precursor, for example 4-oxothiazolidine-carboxylic acid or peptides which are rich in cysteine.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for reducing tissue damage brought about by a metabolic dysfunction in a patient, the method comprising the step of administering to the patient a nutritional composition which comprises a biologically and nutritionally acceptable medium that includes a therapeutically effective amount of cysteine source selected from the group consisting of free cysteine, a cysteine precursor, a cysteine prodrug, protein containing cysteine, and protein hydrolysates containing cysteine, or mixtures thereof, wherein cysteine comprises at least 3% by weight of all amino acids.

2. A method according to claim 1 wherein cysteine comprises at least 3% by weight of all amino acids administered to the patient.

3. A method according to claim 1 wherein the composition includes threonine in an amount providing at least 5% by weight of all amino acids.

4. A method according to claim 1 wherein the composition includes serine in an amount providing at least 12% by weight of all amino acids.

5. A method according to claim 1 wherein the composition includes at least one amino acid chosen from the group consisting of aspartic acid and asparagine.

6. A method according to claim 5 wherein aspartic acid and asparagine are present in an amount providing at least 10% by weight of all amino acids.

7. A method according to claim 1 wherein the composition includes leucine, isoleucine, valine, tryptophan, phenylalanine, lysine, and methionine.

8. A method according to claim 1 wherein the composition includes at least one amino acid chosen from the group consisting of glycine, arginine, taurine and glutamine.

9. A method according to claim 1 in which the cysteine source is chosen from the group consisting of free cysteine, protein hydrolysate, or mixtures thereof.

10. A method according to claim 1 wherein the composition includes:

approximately 5 to about 12 g/l of leucine;
approximately 3 to about 10 g/l of isoleucine;
approximately 5 to about 10 g/l of valine;
approximately 1 to about 3 g/l of tryptophan;
approximately 1.5 to about 7 g/l of phenylalanine;
approximately 2 to about 7 g/l of lysine;
approximately 1.5 to about 5 g/l of methionine; and
approximately 3 to about 7 g/l of threonine.

11. A method according to claim 1 wherein the composition prevents tissue damage caused by a metabolic dysfunction in the patient.

12. A method for treating sepsis or an attack bringing about an inflammatory reaction in a patient, the method comprising the step of administering to the patient a nutritional composition which comprises a biologically and nutritionally acceptable medium that includes a therapeutically effective amount of a cysteine source selected from the group consisting of free cysteine, a cysteine precursor, a cysteine prodrug, protein containing cysteine, and protein hydrolysates containing cysteine, or mixtures thereof, wherein cysteine comprises at least 3% by weight of all amino acids present in the nutritional composition.

13. A method according to claim 12 wherein the composition contains:

approximately 5 to about 12 g/l of leucine;
approximately 3 to about 10 g/l of isoleucine;
approximately 5 to about 10 g/l of valine;
approximately 1 to about 3 g/l of tryptophan;
approximately 1.5 to about 7 g/l of phenylalanine;
approximately 2 to about 7 g/l of lysine;
approximately 1.5 to about 5 g/l of methionine; and
approximately 3 to about 7 g/l of threonine.

14. A nutritional composition for decreasing tissue damage brought about by metabolic dysfunctions in a patient, the composition comprising:

an amino acid source including threonine, serine, aspartic acid, asparagine, and a cysteine source selected from the group consisting of free cysteine, a cysteine precursor, a cysteine prodrug, protein containing cysteine, and protein hydrolysates containing cysteine, or mixtures thereof, in an amount such that cysteine provides at least 3% by weight of all amino acids present in the amino acid source;

a carbohydrate source; and a lipid source.

15. A composition according to claim 14 wherein the amount of nitrogen provided by the cysteine is at least 2.15% by weight of the total nitrogen that is provided by the composition.

16. A composition according to claim 14 wherein threonine comprises at least 5%, by weight, of all the amino acids.

17. A composition according to claim 14 wherein serine comprises at least 12%, by weight, of all the amino acids.

18. A composition according to claim 14 wherein aspartic acid and asparagine each comprise at least 10%, by weight, of all the amino acids.

19. A composition according to claim 14 wherein the amino acid source includes leucine, isoleucine, valine, tryptophan, phenylalanine, lysine, and methionine.

20. A composition according to claim 14 wherein the amino acid source contains:

approximately 5 to about 12 g/l of leucine;
approximately 3 to about 10 g/l of isoleucine;
approximately 5 to about 10 g/l of valine;
approximately 1 to about 3 g/l of tryptophan;
approximately 1.5 to about 7 g/l of phenylalanine;
approximately 2 to about 7 g/l of lysine;
approximately 1.5 to about 5 g/l of methionine; and
approximately 3 to about 7 g/l of threonine.

21. A composition according to claim 14 wherein the amino acid source includes at least one amino acid chosen from a group consisting of glycine, arginine, taurine and glutamine.

22. A composition according to claim 14 wherein the amino acid source is chosen from the group consisting of free amino acids, protein hydrolysate or mixtures thereof.

23. A composition according to claim 14 having a form suitable for enteral administration.

24. A composition according to claim 14 having a form suitable for parenteral administration.

25. A composition according to claim 14 including electrolytes, trace elements and vitamins.

* * * * *